(12) United States Patent
Malamas et al.

(10) Patent No.: US 6,844,358 B2
(45) Date of Patent: Jan. 18, 2005

(54) PHENYL OXO-ACETIC ACIDS USEFUL IN THE TREATMENT OF INSULIN RESISTANCE AND HYPERGLYCEMIA

(75) Inventors: Michael S. Malamas, Jamison, PA (US); Jay E. Wrobel, Lawrenceville, NJ (US); Arlene J. Dietrich, Delran, NJ (US); Zenan Li, Plainsboro, NJ (US); Iwan Gunawan, Somerset, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/300,997

(22) Filed: Nov. 21, 2002

(65) Prior Publication Data

US 2004/0102480 A1 May 27, 2004

Related U.S. Application Data

(62) Division of application No. 09/636,669, filed on Aug. 11, 2000, now Pat. No. 6,509,360, which is a division of application No. 09/307,915, filed on May 10, 1999, now Pat. No. 6,166,069.
(60) Provisional application No. 60/100,435, filed on May 12, 1998, now abandoned.

(51) Int. Cl.[7] .................. A61K 31/44; A61K 31/425; A61K 31/42; C07D 411/00; C07D 405/00
(52) U.S. Cl. .................. 514/336; 514/365; 514/374; 546/280.4; 546/284.7; 549/59; 549/60
(58) Field of Search .................. 546/280.4, 284.7, 546/270.4, 271.4, 272.7; 549/59, 64, 68, 69, 76; 514/336, 59, 60, 365, 374, 397; 548/335.5, 341.5, 341.1, 235, 214

(56) References Cited

FOREIGN PATENT DOCUMENTS

| DE | 3342624 A1 | 3/1984 |
|---|---|---|
| WO | WO 91/11909 | 8/1991 |
| WO | WO 94/22834 | 10/1994 |
| WO | WO 94/22835 | 10/1994 |
| WO | WO 96/09818 | 4/1996 |
| WO | WO 97/21693 | 6/1997 |
| WO | 9725033 | * 7/1997 |

OTHER PUBLICATIONS

Ca 134:178462, "Preparation of [(pyrrolidinoalkoxy)phenyl]benzothiophenes and analogs as thrombin inhibitors", Bastian et. al WO. 9725033.*

* cited by examiner

*Primary Examiner*—Binta Robinson
(74) *Attorney, Agent, or Firm*—Fish & Richardson P.C.

(57) ABSTRACT

This invention provides compounds of Formula I having the structure

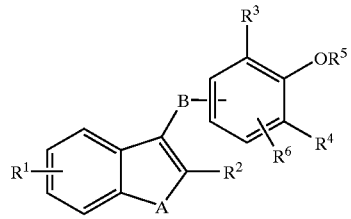

wherein:

A is O, S, or N;
B is —(CH$_2$)$_m$—, —CH(OH)—, or carbonyl;
R$^1$ is hydrogen, halogen, alkyl of 1–6 carbon atoms, alkoxy of 1–6 carbon atoms, or trifluoromethyl;
R$^2$ is alkyl of 1–18 carbon atoms, aryl of 6–10 carbon atoms, arylalkyl of 7–15 carbon atoms, Het-alkyl wherein the alkyl moiety is 1–6 carbon atoms;
Het is

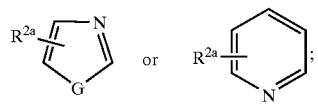

R$^{2a}$ is alkylene of 1–3 carbon atoms;
G is oxygen, sulfur, or nitrogen;
R$^3$, R$^4$ are each, independently, hydrogen, halogen, alkyl of 1–3 carbon atoms, aryl of 6–10 carbon atoms or a heterocyclic ring of 5 to 7 ring atom containing 1 to 3 heteroatoms selected from oxygen, nitrogen, sulfur;
R$^5$ is hydrogen, alkyl of 1–6 carbon atoms, —CH(R$^7$)R$^8$, —C(CH$_2$)$_n$CO$_2$R$^9$, —C(CH$_3$)$_2$CO$_2$R$^9$, —CH(R$^7$)(CH$_2$)$_n$CO$_2$R$^9$, or CH(R$^7$)C$_6$H$_4$CO$_2$R$^9$;
R$^6$ is hydrogen, halogen, alkyl of 1–6 carbon atoms, or —OR$^5$;
m=1–6;
n=1–6;
R$^7$ is hydrogen, alkyl of 1–6 carbon atoms, aryl of 6–10 carbon atoms, or arylalkyl of 7–15 carbon atoms;
R$^8$ is —CO$_2$R$^{10}$, —CONHR$^{10}$, tetrazole, or —PO$_3$;
R$^9$ and R$^{10}$ are each, independently, hydrogen, alkyl of 1–6 carbon atoms, aryl of 6–10 carbon atoms, or arylalkyl of 7–15 carbon atoms;

or a pharmaceutically acceptable salt thereof, which are useful in treating metabolic disorders related to insulin resistance or hyperglycemia.

2 Claims, No Drawings

PHENYL OXO-ACETIC ACIDS USEFUL IN THE TREATMENT OF INSULIN RESISTANCE AND HYPERGLYCEMIA

This application claims the benefit of U.S. Provisional Application No. 60/100,435, which was converted from U.S. patent application Ser. No. 09/076,596, filed May 12, 1998, pursuant to a petition filed under 37 C.F.R. 1.53(c)(2)(i) on May 11, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPa and SH-PTP2 (B. J. Goldstein, *J. Cellular Biochemistry* 1992, 48, 33; B. J. Goldstein, *Receptor* 1993, 3, 1–15; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

Eur. Pat. Appl. 425359 A1 discloses the preparation of 3-benzoylbenzofuran derivatives as cardiovascular drug intermediates. Czech. Patent 265559 B1 discloses a process for preparing 2-ethyl-3-(3,5-dibromo-4-hydroxybenzoyl) coumarone as an uricosuric agent. Fodor discloses 2-Ethyl-3-(3,5-dibromo-4-hydroxybenzoyl)benzofuran [HU 18236 (1980)].

DESCRIPTION OF THE INVENTION

This invention provides a compound of formula I having the structure

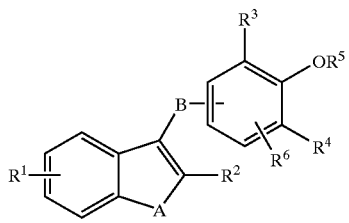

I wherein:
A is O, S, or N;
B is —(CH$_2$)$_m$—, —CH(OH)—, or carbonyl;
R$^1$ is hydrogen, nitro, halogen, alkyl of 1–6 carbon atoms, alkoxy of 1–6 carbon atoms, or trifluoromethyl;
R$^2$ is alkyl of 1–18 carbon atoms, aryl of 6–10 carbon atoms, arylalkyl of 7–15 carbon atoms, Het-alkyl wherein the alkyl moiety is 1–6 carbon atoms;
Het is

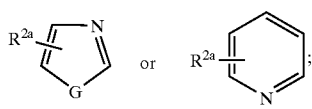

R$^{2a}$ is alkylene of 1–3 carbon atoms;
G is oxygen, sulfur, or nitrogen;
R$^3$, R$^4$ are each, independently, hydrogen, halogen, alkyl of 1–3 carbon atoms, aryl of 6–10 carbon atoms or a heterocyclic ring of 5 to 7 ring atom containing 1 to 3 heteroatoms selected from oxygen, nitrogen, sulfur;
R$^5$ is hydrogen, alkyl of 1–6 carbon atoms, —CH(R$^7$)R$^8$, —C(CH$_2$)$_n$CO$_2$R$^9$, —C(CH$_3$)$_2$CO$_2$R$^9$, —CH(R$^7$)(CH$_2$)$_n$CO$_2$R$^9$, or CH(R$^7$)C$_6$H$_4$CO$_2$R$^9$;
R$^6$ is hydrogen, halogen, alkyl of 1–6 carbon atoms, or —OR$^5$;
m=1–6;
n=1–6;
R$^7$ is hydrogen, alkyl of 1–6 carbon atoms, aryl of 6–10 carbon atoms, or arylalkyl of 7–15 carbon atoms;
R$^8$ is —CO$_2$R$^{10}$, —CONHR$^{10}$, tetrazole, or —PO$_3$H$_2$
R$^9$ and R$^{10}$ are each, independently, hydrogen, alkyl of 1–6 carbon atoms, aryl of 6–10 carbon atoms, or arylalkyl of 7–15 carbon atoms;
or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Alkyl includes both straight chain as well as branched moieties. Halogen means bromine, chlorine, fluorine, and iodine. It is preferred that the aryl portion of the aryl or aralkyl substituent is a phenyl, naphthyl or 1,4-benzodioxan-5-yl group; with phenyl being most preferred. The aryl moiety may be optionally mono-, di-, or tri-substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are those compounds of Formula I, wherein
R$^1$ is hydrogen or halogen;
R$^2$ is alkyl of 1–6 carbon atoms or aralkyl of 7–15 carbon atoms;
R$^3$ and R$^4$ are halogen; and
m=1
or a pharmaceutically acceptable salt thereof.

More preferred compounds of the present invention are set forth below:

Example 1. (2-ethyl-benzofuran-3-yl)-(3,5-dibromo-4-hydroxy-phenyl)-methanone
Example 2. [2,6-dibromo-4-(2-ethyl-benzofuran-3-carbonyl)-phenoxy]-acetic acid
Example 3. 2,6-dibromo-4-(2-ethyl-benzofuran-3-yl-methyl)-phenol
Example 4. (3,5-dibromo-2,4-dihydroxy-phenyl)-(2-ethyl-benzofuran-3-yl)-methanone
Example 5. [2,6-dibromo-4-(2-butyl-benzofuran-3-carbonyl)-phenoxy]-acetic acid
Example 6. (2-butyl-benzofuran-3-yl)-(3,5-dibromo-4-dihydroxy-phenyl)-methanone
Example 7. [2,6-dibromo-4-(2-butyl-benzofuran-3-ylmethyl)-phenoxy]-acetic acid
Example 8. (2-ethyl-benzofuran-3-yl)-(2,4,6-tribromo-3-hydroxy-phenyl)-methanone
Example 9. (2-benzyl-benzofuran-3-yl)-(4-hydroxy-3,5-diiodo-phenyl)-methanone
Example 10. [4-(2-benzyl-benzofuran-3-carbonyl)-2,6-dibromo-phenoxy]-acetic acid
Example 11. (2-benzyl-benzo[b]thiophen-3-yl)-(3,5-dibromo-4-hydroxy-phenyl)-methanone
Example 12. [4-(2-benzyl-benzo[b]thiophen-3-carbonyl)-2,6-dibromo-phenoxy]-acetic acid
Example 13. (5-chloro-2-ethyl-benzofuran-3-yl)-(3,5-dibromo-4-hydroxy-phenyl)-methanone
Example 14. (2-benzyl-benzofuran-3-yl)-(3,5-dibromo-4-hydroxy-phenyl)-methanone
Example 15. (3,5-dibromo-4-hydroxy-phenyl)-(2-phenethyl-benzofuran-3-yl)-methanone
Example 16. (2-butyl-benzofuran-3-yl)-(4-hydroxy-3,5-diiodo-phenyl)-methanone
Example 17. [4-(2-benzyl-benzofuran-3-carbonyl)-2,6-diiodo-phenoxy]-acetic acid
Example 18. (2-ethyl-benzofuran-3-yl)-(4-hydroxy-3,5-diiodo-phenyl)-methanone Example 19. [2,6-dibromo-4-(2-phenethyl-benzofuran-3-carbonyl)-phenoxy]-acetic acid Example 20. [2,6-dibromo-4-(5-chloro-2-ethyl-1-benzofuran-3-carbonyl)-phenoxy]-acetic acid Example 21. [4-(2-benzyl-benzo[b]thiophene-3-carbonyl)-2,6-dibromo-phenoxymethyl]-phosphonic acid Example 22. (R)-2-[2,6-dibromo-4-(2-butyl-benzofuran-3-carbonyl)-phenoxy]-3-phenyl-propionic acid Example 23. (R)-2-[2,6-dibromo-4-(2-butyl-benzofuran-3-ylmethyl)-phenoxy]-3-phenyl-propionic acid The compounds of this invention were prepared according to the following scheme from commercially available starting materials or starting materials which can be prepared using literature procedures. Scheme I shows the preparation of representative compounds of this invention.

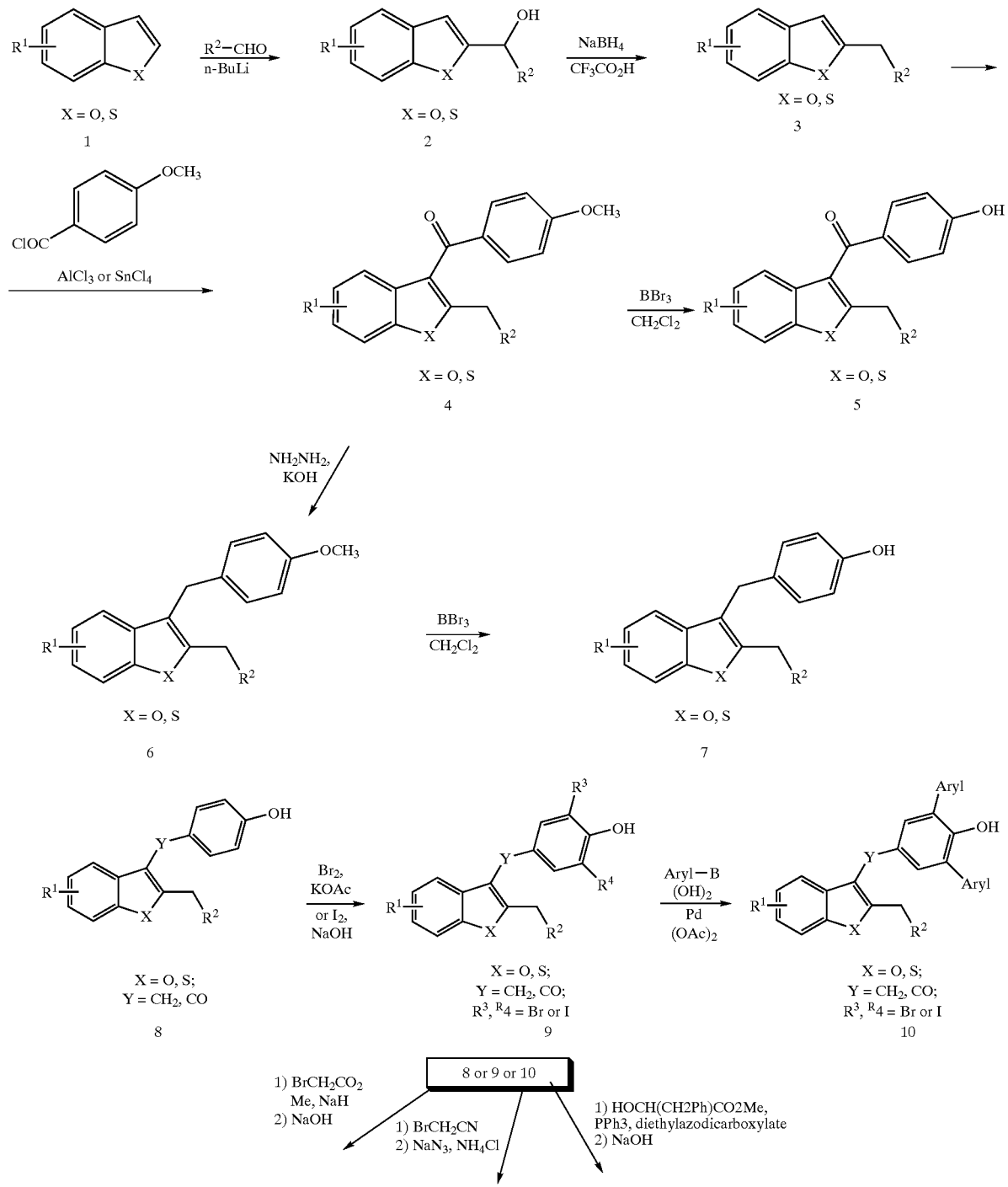

-continued

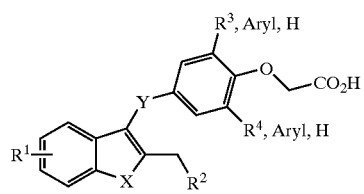

X = O, S;
Y = CH₂, CO;
R³, R⁴ = Br or I
11

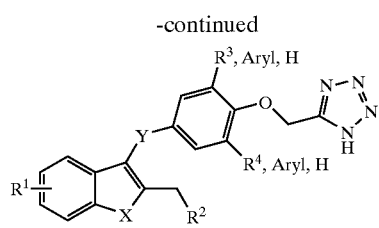

X = O, S;
Y = CH₂, CO;
R³, R⁴ = Br or I
12

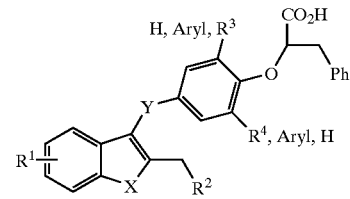

X = O, S;
Y = CH₂, CO;
R³, R⁴ = Br or I
13

In Scheme I, commercially available benzofurans and benzothiophenes (1) can be lithiated at 2-position with alkyllithium reagents which upon treatment with aldehydes R²—CHO produces alcohols (2) [ref. Org. React. 1979, volume 26]. Reduction of alcohols (2) with sodium borohydride and trifluoroacetic acid [ref. Syn. Comm. 1990, 20, 487–493] afforded compounds (3). Compounds (3) can be treated with acyl-chlorides using the Friedel-Crafts protocol [Friedel-Crafts and Related Reactions, Wiley Interscience, New York, 1963–1965] to produce ketones (4). Ketones can be reduced to compounds (6) using the Wolff-Kishner protocol [ref. Org. Reactions, 1948, volume 4]. Compound (4) and (6) can be demethylated with BBr₃ [ref. J. Org. Chem. 1974, 39, 1427–1429] to produce phenols (5) and (7). Phenols (5) and (7) can be brominated with bromine and potassium acetate in acetic acid or iodinated with iodine in the presence of sodium hydroxide to produce the brominated or iodinated compounds (9). Compounds (9) can be coupled with aromatic or heteroaromatic boronic acids in the presence of palladium catalysts [Suzuki protocol; ref. Syn. Comm. 1981, 11, 513–519] to produce terphenyls (10). Compounds (5), (7), (9), and (10) can be used to produce the desired products (11–13). First, compounds (5), (7), and (9) can be alkylated with methyl bromoacetate in the presence of sodium hydride, to produce oxo-acetic acids methyl esters, that can be saponified with sodium hydroxide to produce the oxo-acetic acids (11). Secondly, compounds (5), (7), and (9) can be alkylated with bromoacetonitrile to produce oxo-acetonitrile, that upon treatment with sodium azide and ammonium chloride produce tetarzoles (12). Thirdly, compounds (5), (7), and (9) can be treated with 2-hydroxy carboxylates (for example 3-phenyllactic acid) using the Mitsunobu protocol [ref. *Synthesis*. 1981, 1–27] to produce oxo-acetates, that can be saponified with sodium hydroxide to afford oxo-acetic acids (13).

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following two standard pharmacological test procedures which measure the inhibition of PTPase.

Inhibition of Tri-phosphorylated Insulin Receptor Dodecaphosphopeptide Dephosphorylation by Rat Hepatic Protein-tyrosine Phosphatases (PTPases)

This standard pharmacological test procedure assess the inhibition of rat hepatic microsomal PTPase activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly outlined below.

Preparation of Microsomal Fraction

Rats (Male Sprague-Dawley rats (Charles River, Kingston, N.Y.) weighing 100–150 g, maintained on standard rodent chow (Purina)) are sacrificed by asphyxiation with CO₂ and bilateral thoracotomy. The liver is removed and washed in cold 0.85% (w/v) saline and weighed. The tissue is homogenized on ice in 10 volumes of Buffer A and the microsomes are isolated essentially as described by Meyerovitch J, Rothenberg P, Shechter Y, Bonner-Weir S, Kahn C R. Vanadate normalizes hyperglycemia in two mouse models of non-insulin-dependent diabetes mellitus. *J Clin Invest* 1991; 87:1286–1294 and Alberts B, Bray D, Lewis J, Raff M, Roberts K, Watson J D, editors. Molecular biology of the cell. New York: Garland Publishing, Inc., 1989 with minor modifications. The liver homogenate is filtered through silk to remove any remaining tissue debris and then is centrifuged at 10,000×g for 20 minutes at 40 C. The supernatant is decanted and centrifuged at 100,000×g for 60 minutes at 40 C. The pellet, microsomes and small vesicles, is resuspended and lightly homogenized in: 20 mM TRIS-HCl (pH 7.4), 50 ml 2-mercaptoethanol, 250 mM sucrose, 2 mM EDTA, 10 mM EGTA, 2 mM AEBSF, 0.1 mM TLCK, 0.1 mM TPCK, 0.5 mM benzamidine, 25 ug/ml leupeptin, 5 ug/ml pepstatin A, 5 ug/ml;H5B antipain, 5 ug/ml chymostatin, 10 ug/ml aprotinin (Buffer A), to a final concentration of approximately 850 ug protein/ml. Protein concentration is determined by the Pierce Coomassie Plus Protein Assay using crystalline bovine serum albumin as a standard (Pierce Chemical Co., Rockford, Ill.).

Measurement of PTPase Activity

The malachite green-ammonium molybdate method, as described by Lanzetta P A, Alvarez L J, Reinach P S, Candia O A was used. An improved assay for nanomolar amounts of inorganic phosphate. *Anal. Biochem.* 1979;100:95–97, and adapted for the platereader, is used for the nanomolar detection of liberated phosphate by rat hepatic microsomal PTPases. The test procedure uses, as substrate, a dodeca-phosphopeptide custom synthesized by AnaSpec, Inc. (San Jose, Calif.). The peptide, TRDIYETDYYRK, corresponding to the 1142–1153 catalytic domain of the insulin receptor, is tyrosine phosphorylated on the 1146, 1150 and 1151 tyrosine residues. The microsomal fraction (83.25 ul) is preincubated for 10 min at 37 deg. C. with or without test compound (6.25 ul) and 305.5 ul of the 81.83 mM HEPES reaction buffer, pH 7.4. Peptide substrate, 10.5 ul at a final concentration of 50 uM, is equilibrated to 37 deg. C. in a LABLINE Multi-Blok heater equipped with a titerplate adapter. The preincubated microsomal preparation (39.5 ul) with or without drug is added to initiate the dephosphorylation reaction, which proceeds at 37 deg. C. for 30 min. The reaction is terminated by the addition of 200 ul of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 ul MG/AM/Tw to substrate and followed by 39.5 ul of the preincubated membrane with or without drug. The color is allowed to develop at room temperature for 30 min and the sample absorbances are determined at 650 nm using a platereader (Molecular Devices). Samples and blanks are prepared in quadruplicates. Screening activity of 50 uM (final) drug is accessed for inhibition of microsomal PTPases.

Calculations

PTPase activities, based on a potassium phosphate standard curve, are expressed as nmoles of phosphate released/min/mg protein. Test compound PTPase inhibition is calculated as percent of control. A four parameter non-linear logistic regression of PTPase activities using SAS release 6.08, PROC NLIN, is used for determining IC50 values of test compounds. All compounds were administered at a concentration of 50 $\mu$M. The following results were obtained using representative compounds of this invention.

| Example | IC$_{50}$ ($\mu$M) | % Change from Control at 50 $\mu$M |
|---|---|---|
| 1 | 70.1 | |
| 2 | | −25 |
| 3 | | −34 |
| 4 | 34.3 | |
| 5 | 31.2 | |
| 6 | 24.2 | |
| 7 | 22.7 | |
| 8 | 17.5 | |
| 9 | 22.7 | |
| 10 | 36 | |
| 11 | 33.9 | |
| 12 | 27.8 | |
| 13 | 27.1 | |
| 14 | 27.8 | |
| 15 | 20.5 | |
| 16 | 15.3 | |
| 17 | 28.4 | |
| 18 | 30.7 | |
| 19 | 26.3 | |
| 20 | 40.4 | |
| 21 | 34.5 | |
| 22 | | −77 |
| 23 | | −85 |
| phenylarsine oxide (Reference) | | −57 |

Inhibition of Tri-Phosphorylated Insulin Receptor Dodecaphosphopeptide Dephosphorylation by hPTP1B This standard pharmacological test procedure assess the inhibition of recombinant rat protein tyrosine phosphatase, PTP1B, activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly described below.

Human recombinant PTP1B was prepared as described by Goldstein (see Goldstein et al. *Mol. Cell. Biochem.* 109, 107, 1992). The enzyme preparation used was in microtubes containing 500–700 $\mu$g/ml protein in 33 mM Tris-HCl, 2 mM EDTA, 10% glycerol and 10 mM 2-mercaptoethanol.

Measurement of PTPase Activity

The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The test procedure uses, as substrate, a dodecaphosphopeptide custom synthesized by AnaSpec, Inc. (San Jose, Calif.). the peptide, TRDIYETDYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 mM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.5 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AM/Tw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in quadruplicates.

Calculations

PTPase activities, based on a potassium phosphate standard curve, are expressed as nmoles of phosphate released/min/mg protein. Inhibition of recombinant PTP1B by test compounds is calculated as percent of phosphatase control. A four parameter non-linear logistic regression of PTPase activities using SAS release 6.08, PROC NLIN, is used for determining IC$_{50}$ values of test compounds. The following results were obtained.

| Example | % change from control at 10 $\mu$M | IC50 ($\mu$M) |
|---|---|---|
| 1 | | 25.8 (rPTP1B) |
| 2 | −30 (rPTP1B) | |
| 3 | −74 (rPTP1B) | |
| 4 | −64 (rPTP1B) | |
| 5 | −78 (rPTP1B) | |
| 6 | −90 (rPTP1B) | |
| 7 | −99 (rPTP1B) | |
| 7 | | 1.4 (hPTP1B) |
| 8 | −61 (rPTP1B) | |
| 9 | −99 (rPTP1B) | |
| 10 | −75 (rPTP1B) | |
| 11 | | 3.97 (rPTP1B) |
| 11 | | 1.94 (hPTP1B) |
| 12 | −88 (rPTP1B) | |
| 13 | −64 (rPTP1B) | |
| 14 | −81 (rPTP1B) | |
| 15 | | 2.6 (rPTP1B) |
| 16 | | 0.19 (rPTP1B) |
| 16 | | 2.6 (hPTP1B) |
| 17 | −97 (rPTP1B) | |
| 18 | −60 (rPTP1B) | |

-continued

| Example | % change from control at 10 μM | IC50 (μM) |
|---|---|---|
| 19 | −53 (rPTP1B) | |
| 20 | −34 (rPTP1B) | |
| 21 | −35 (rPTP1B) | |
| 22 | | 1.15 (hPTP1B) |
| 23 | | 0.87 (hPTP1B) |
| Phenylarsine oxide (reference standard) | 39.7 | |
| Sodium orthovanadate (reference standard) | 244.8 | |
| Ammonium molybdate tetrahydrate (reference standard) | 8.7 | |

The blood glucose lowering activity of representative compounds of this invention were demonstrated in an in vivo standard procedure using diabetic (ob/ob) mice. The procedures used and results obtained are briefly described below.

The non-insulin dependent diabetic (NIDDM) syndrome can be typically characterizes by obesity, hyperglycemia, abnormal insulin secretion, hyperinsulinemia and insulin resistance. The genetically obese-hyperglycemic ob/ob mouse exhibits many of these metabolic abnormalities and is thought to be a useful model to search for hypoglycemic agents to treat NIDDM [Coleman, D.: Diabetologia 14: 141–148, 1978].

In each test procedure, mice [Male or female ob/ob (C57 B1/6J) and their lean litermates (ob/+ or +/+, Jackson Laboratories) ages 2 to 5 months (10 to 65 g)] of a similar age were randomized according to body weight into 4 groups of 10 mice. The mice were housed 5 per cage and are maintained on normal rodent chow with water ad libitum. Mice received test compound daily by gavage (suspended in 0.5 ml of 0.5% methyl cellulose); dissolved in the drinking water; or admixed in the diet. The dose of compounds given ranges from 2.5 to 200 mg/kg body weight/day. The dose is calculated based on the fed weekly body weight and is expressed as active moiety. The positive control, ciglitazone (5-(4-(1-methylcyclohexylmethoxy)benzyl)-2,4-dione, see Chang, A., Wyse, B., Gilchrist, B., Peterson, T. and Diani, A. Diabetes 32: 830–838, 1983.) was given at a dose of 100 mg/kg/day, which produces a significant lowering in plasma glucose. Control mice received vehicle only.

On the morning of Day 4, 7 or 14 two drops of blood (approximetly 50 ul) were collected into sodium fluoride containing tubes either from the tail vein or after decapitation. For those studies in which the compound was administered daily by gavage the blood samples were collected two hours after compound administration. The plasma was isolated by centrifugation and the concentration of glucose is measured enzymatically on an Abbott V.P. Analyzer.

For each mouse, the percentage change in plasma glucose on Day 4, 7 or 14 is calculated relative to the mean plasma glucose of the vehicle treated mice. Analysis of variance followed by Dunett's Comparison Test (one-tailed) are used to estimate the significant difference between the plasma glucose values from the control group and the individual compound treated groups (CMS SAS Release 5.18).

The results shown in the table below shows that the compounds of this invention are antihyperglycemic agents as they lower blood glucose levels in diabetic mice.

| Example | Dose (mg/Kg) | % Change Glucose from Vehicle | % Change Insulin from Vehicle |
|---|---|---|---|
| 1 | 100 | −44.6 | −89.5 |
| 2 | 100 | −48.1 | −78.2 |
| 3 | 100 | −6.2a | −56.6 |
| 4 | 100 | −19.8a | −61.8 |
| 5 | 100 | −20.1 | −54.8 |
| 6 | 100 | −40.6 | −70.4 |
| 7 | 100 | −29.4 | −13.1a |
| 8 | 100 | −3.3a | −31.2 |
| 9 | 100 | −37.1 | −73.7 |
| 10 | 100 | −17.7a | −70.0 |
| 11 | 100 | −30.3 | −53.2 |
| 12 | 100 | −30.7 | −60.7 |
| 13 | 100 | −12a | −74.5 |
| 14 | 100 | −36.8 | −40.7a |
| 15 | 100 | −32.8 | −10.3a |
| 16 | 100 | −51.8 | −73.7 |
| 18 | 100 | −39.6 | −83.6 |
| Ciglitazone (reference standard | 100 | −43 | −39 | a no significant activity (p < 0.05) at this dose.

Based on the results obtained in the standard pharmacological test procedures, representative compounds of this invention have been shown to inhibit PTPase activity and lower blood glucose levels in diabetic mice, and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

(2-Ethyl-benzofuran-3-yl)-(3,5-dibromo-4-hydroxy-phenyl)-methanone

This compound was obtained from Sigma Chemicals.

EXAMPLE 2

[2,6-dibromo-4-(2-ethyl-benzofuran-3-carbonyl)-phenoxy]-acetic acid tert-Butyl bromoacetate (0.57 mL, 3.54 mmol) was added dropwise into a mixture of (2-ethyl-benzofuran-3-yl)-(3,5-dibromo-4-hydroxy-phenyl)-methanone (1.0 g, 2.36 mmol), potassium carbonate (0.98 g, 7.08 mmol), and N,N-dimethylformamide (10 mL). The mixture was stirred at 80° C. for 3 hours, poured into water and extracted with ethyl acetate. The organic extracts were dried over $MgSO_4$. Evaporation gave a yellow oil (1.4 g) which was taken in dichloromethane (50 mL) and treated with trifluoroacetic acid (5 mL) for 10 hours. The volatiles were removed in vacuo and the residue was purified by flash chromatography on acidic silica gel (hexane/EtoAc 1:1) to give a white solid (0.82 g, 42% yield): mp 135–137; MS m/e 480 $M^+$;

Analysis for: $C_{19}H_{14}Br_2O_5$ Calc'd: C, 47.33; H, 2.93. Found: C, 47.25; H, 2.91

EXAMPLE 3

2,6-Dibromo-4-(2-ethyl-benzofuran-3-yl-methyl)-phenol tert-Butyldimethylsilyl chloride was added in to a mixture of (2-ethyl-benzofuran-3-yl)-(3,5-dibromo-4-hydroxy-phenyl)-methanone (10.0 g, 23.58 mmol), imidazole (1.6 g, 23.58 mmol), 4-dimethylaminopyridine (100 mg) and N,N-dimethylformamide (100 mL). The mixture was stirred at room temperature for 10 hours, poured into water, and extracted with ethyl acetate. The organic extracts were dried over $MgSO_4$. Evaporation gave an oil (11.5 g) which was taken in MeOH (100 mL) and treated with sodium borohydride (0.96 g, 25.65 mmol). The mixture was stirred at room temperature for 3 hours poured into water and extracted with ethyl ether. The organic extracts were dried over $MgSO_4$. Evaporation gave a residue (10.5 g) which was taken in dichloromethane (100 mL) and treated at 0° C. with triethylsilane (6.21 mL, 38.9 mmol) and trifluoroacetic acid (10 mL). After stirring for 30 minutes the volatiles were removed in vacuo and the residue was treated with hydrofluoric acid (5.0 mL) in acetonitrile (50 mL) at 80° C. for 5 hours. The volatiles were removed in vacuo and the residue was purified by flash chromatography (hexane/ethyl acetate 10:1) to give a white solid (6.5 g, 37% yield): mp 87–88; MS m/e 408 $M^+$;

EXAMPLE 4

(3,5-Dibromo-2,4-dihydroxy-phenyl)-(2-ethyl-benzofuran-3-yl)-methanone

A soultion of bromine (0.73 mL, 14.2 mmol) in acetic acid (3 mL) was added to a solution of the known compound (2,4-dihydroxy-phenyl)-(2-ethyl-benzofuran-3-yl)-methanone (CA reg. no. 90908-66-0) (2.0 g, 7.08 mmol) in 6:1 acetic acid:water (14 mL). The reaction mixture was added to water (200 mL) and filtered to provide the title co pound as a tan solid (2.7 g, 87%): mp 150–151; MS m/e 438 $M^+$;

Analysis for: $C_{17}H_{12}Br_2O_4$ Calc'd: C, 46.39; H, 2.75. Found: C, 45.95; H, 2.66

EXAMPLE 5

[2,6-Dibromo-4-(2-butyl-benzofuran-3-carbonyl)-phenoxy]-acetic acid

This compound was prepared from (2-butyl-benzofuran-3-yl)-(3,5-dibromo-4-hydroxy-phenyl)-methanone and tert-butyl bromoacetate in substantially the same manner, as described in Example 2, and was obtained as an off-white solid, mp 92–94° C.; MS m/e 508 ($M^+$);

Analysis for: $C_{21}H_{18}Br_2O_5$ Calc'd: C, 49.44; H, 3.56. Found: C, 47.24; H, 3.59

EXAMPLE 6

(2-Butyl-benzofuran-3-yl)-(3,5-dibromo-4-dihydroxy-phenyl)-methanone

Bromine (3.49 mL) was added dropwise into a mixture of 2-n-butyl-3-(hydroxybenzoyl)benzo[b]furan (10.0 g, 34.0 mmol) acetic acid (50 mL) and $H_2O$ (10 mL). The mixture was stirred for 12 hours and poured into water. The precipitated solid was filtered and dried to give a white solid (11.2 g, 71% yield): mp 95–97; MS m/e 450 $M^+$;

Analysis for: $C_{19}H_{16}Br_2O_3 \times 0.8\ H_2O$ Calc'd: C, 48.89; H, 3.80. Found: C, 48.83; H, 3.37

EXAMPLE 7

2,6-Dibromo-4-(2-butyl-benzofuran-3-ylmethyl)-phenoxy]-acetic acid

This compound was prepared from 2,6-dibromo-4-(2-ethyl-benzofuran-3-yl-methyl)-phenol and tert-butyl bromoacetate in substantially the same manner, as described in Example 2, and was obtained as an off-white solid, mp 118–119° C.; MS m/e 494 ($M^+$);

Analysis for: $C_{21}H_{20}Br_2O_4$ Calc'd: C, 50.83; H, 4.06. Found: C, 50.46; H, 3.94

EXAMPLE 8

(2-Ethyl-benzofuran-3-yl)-(2,4,6-tribromo-3-hydroxy-phenyl)-methanone

This compound was prepared from (2-ethyl-benzofuran-3-yl)-(3-hydroxy-phenyl)-methanone and bromine in substantially the same manner, as described in Example 6, and was obtained as a white solid, mp 153–154° C.; MS m/e 517 (M–H)$^+$;

Analysis for: $C_{17}H_{11}Br_3O_3$ Calc'd: C, 40.52; H, 2.20. Found: C, 40.12; H, 2.07

EXAMPLE 9

(2-Benzyl-benzofuran-3-yl)-(4-hydroxy-3,5-diiodo-phenyl)-methanone

A solution of (2-benzyl-benzofuran-3-yl)-(4-hydroxyphenyl)-methanone (2.48 g, 7.55 mmol) in sodium hydroxide (1.2 g) and water (113 mL) was added dropwise into a mixture of iodine (4.22 g), sodium iodide (2.75 g) and water (113 mL). The new mixture was stirred at 65° C. for 3 hours. The mixture was poured into water and extracted with ethyl acetate. The organic extracts were dried over $MgSO_4$. Evaporation and purification by flash chromatography (petroleum ether/ethyl acetate 6:4) gave a tan solid (1.92 g, 4% yield): mp 153–154° C.; MS m/e 580 (M$^+$);

Analysis for: $C_{22}H_{14}I_2O_3$ Calc'd: C, 45.55; H, 2.43. Found: C, 46.23; H, 2.36

EXAMPLE 10

[4-(2-Benzyl-benzofuran-3-carbonyl)-2,6-dibromo-phenoxy]-acetic acid

This compound was prepared from (2-benzyl-benzofuran-3-yl)-(4-hydroxy-phenyl)-methanone and methyl bromoacetate in substantially the same manner, as described in Example 20, and was obtained as an off-white solid, mp 165–167° C.; MS m/e 544 (M)$^+$;

Analysis for: $C_{24}H_{16}Br_2O_5$ Calc'd: C, 52.97; H, 2.96. Found: C, 52.74; H, 2.94

EXAMPLE 11

(2-Benzyl-benzo[b]thiophen-3-yl)-(3,5-dibromo-4-hydroxy-phenyl)-methanone

The known compound, 2-benzyl-benzo[b]thiophene (CA reg. no. 3407-15-6) was acylated with one equilvalent of anisoyl chloride using one equivalent of a tin (IV) chloride promoter in carbon disulfide solvent to afford (2-benzyl-benzo[b]thiophen-3-yl)-(4-methoxy-phenyl)-methanone (85% yield). This compound was demethylated using six equivalents of pyridinium hydrocholide at 228° C. to afford (2-benzyl-benzo[b]thiophen-3-yl)-(4-hydroxy-phenyl)-methanone (90% yield). This compound was brominated according to the procedure in Example 4 to afford the tide compound as a white solid (95% yield): mp 155.5–156.5; MS m/e 500 (M)$^+$;

Analysis for: $C_{22}H_{14}Br_2O_2S$ Calc'd: C, 52.61; H, 2.80. Found: C, 52.43; H, 2.71

EXAMPLE 12

[4-(2-Benzyl-benzo[b]thiophen-3-carbonyl)-2,6-dibromo-phenoxy]-acetic acid

This compound was prepared from (2-benzyl-benzo[b]thiophen-3-yl)-(3,5-dibromo-4-hydroxy-phenyl)-methanone and methyl bromoacetate in substantially the same manner, as described in Example 20, and was obtained as an off-white solid, mp 162–163° C.; MS m/e 558 (M)$^+$;

Analysis for: $C_{24}H_{16}Br_2O_4S$ Calc'd: C, 51.45; H, 2.88. Found: C, 51.15; H, 2.71

EXAMPLE 13

(5-Chloro-2-ethyl-benzofuran-3-yl)-(3,5-dibromo-4-hydroxy-phenyl)-methanone

This compound was prepared from (5-chloro-2ethyl-benzofuran-3-yl)-(4-hydroxy-phenyl)-methanone and bromine in substantially the same manner, as described in Example 6, and was obtained as a white solid, mp 126–128° C.; MS m/e 454.9 (M–H)$^+$;

Analysis for: $C_{17}H_{11}Br_2ClO_3$ Calc'd: C, 44.53; H, 2.42. Found: C, 44.35; H, 2.13

EXAMPLE 14

(2-Benzyl-benzofuran-3-yl)-(3,5-dibromo-4-hydroxy-phenyl)-methanone

This compound was prepared from (2-benzyl-benzofuran-3-yl)-(4-hydroxy-phenyl)-methanone and bromine in substantially the same manner, as described in Example 6, and was obtained as an off-white solid, mp 156–158° C.; MS m/e 484 (M$^+$);

Analysis for: $C_{22}H_{14}Br_2O_3$ Calc'd: C, 53.43; H, 2.74. Found: C, 53.73; H, 2.75

EXAMPLE 15

(3,5-Dibromo-4-hydroxy-phenyl)-(2-phenethyl-benzofuran-3-yl)-methanone

This compound was prepared from (2-phenethyl-benzofuran-3-yl)-(4-hydroxy-phenyl)-methanone and bromine in substantially the same manner, as described in Example 6, and was obtained as a yellow solid, mp 153–154° C.; MS m/e 502 (M+H)$^+$;

Analysis for: $C_{23}H_{16}Br_2O_3 \times 0.057\ C_2H_4O_2$ Calc'd: C, 55.12; H, 3.25. Found: C, 54.72; H, 2.99

EXAMPLE 16

(2-Butyl-benzofuran-3-yl)-(4-hydroxy-3,5-diiodo-phenyl)-methanone

Known Compound (CA reg. no. 1951-26-4): mp 141.5–142.5° C.; MS m/e 545 (M+H)$^+$;

Analysis for: $C_{19}H_{16}I_2O_3$ Calc'd: C, 41.79; H, 2.95. Found: C, 41.97; H, 2.83

EXAMPLE 17

[4-(2-Benzyl-benzofuran-3-carbonyl)-2,6-diiodo-phenoxy]-acetic acid

This compound was prepared from (2-benzyl-benzofuran-3-yl)-(3,5-diiodo-4-hydroxy-phenyl)-methanone and tert-butyl bromoacetate in substantially the same manner, as described in Example 2. Formic acid was used in the place of trifluoroacetic acid. The product was obtained as an off-white solid, mp 144–146° C.; MS m/e 638 (M$^+$);

Analysis for: $C_{24}H_{16}I_2O_5$ Calc'd: C, 45.17; H, 2.53. Found: C, 44.19; H, 2.42

EXAMPLE 18

[4-(2-Benzyl-benzo[b]thiophen-3-carbonyl)-2.6-dibromo-phenoxy]-acetic acid

Known compound (CA reg. no. 68-90-6).

EXAMPLE 19

[2,6-Dibromo-4-(2-phenethyl-benzofuran-3-carbonyl)-phenoxy]-acetic acid

This compound was prepared from (2-phenethyl-benzofuran-3-yl)-(3,5-dibromo-4-hydroxy-phenyl)- methanone in substantially the same manner, as described in Example 20, and was obtained as a white solid, mp 163–164° C.; MS m/e 556 (M+);

Analysis for: $C_{25}H_{18}Br_2O_5$ Calc'd: C, 53.79; H, 3.25. Found: C, 53.91; H, 3.14

EXAMPLE 20

[2,6-Dibromo-4-(5-chloro-2-ethyl-1-benzofuran-3-carbonyl)-phenoxy]-acetic

Step a) [2,6-Dibromo-4-(5-chloro-2-ethyl-1-benzofuran-3-carbonyl)-phenoxy]-acetic acid methyl ester Methyl bromoacetate was added dropwise into a mixture of (4-chloro-2-ethyl-benzofuran-3-yl)-(3,5-dibromo-4-hydroxy-phenyl)-methanone (2.81 g, 6.13 mmol), potassium carbonate (0.93 g) and N,N-dimethylformamide (28 mL). The mixture was stirred for 15 hours poured into water and extracted with ethyl acetate. The organic extracts were dried over MgSO$_4$. Evaporation and purification by flash chromatography (petroleum ether/ethyl acetate 9:1) gave a white solid (2.89 g, 89% yield): mp 108–109° C.; MS m/e 528 (M+);

Analysis for: $C_{20}H_{51}Br_2ClO_5$ Calc'd: C, 45.27; H, 2.89. Found: C, 45.08; H, 2.61

Step b) [2,6-Dibromo-4-(5-chloro-2-ethyl-1-benzofuran-3-carbonyl)-phenoxy]-acetic Potassium hydroxide (15.9 mL, 0.5 N) was added into a solution of [2,6-dibromo-4-(5-chloro-2-ethyl-1-benzofuran-3-carbonyl)-phenoxy]-acetic acid methyl ester (2.8 g, 5.3 mmol) in tetrahydrofuran (20 mL) and methyl alcohol (20 mL). The mixture was stirred for 30 minutes poured into water, acidified with HCl, and cooled to 0° C. The precipitated solid filtered and dried. The crude product was recrystallized from acetic acid and water to yield a white solid (2.01 g, 74% yield): mp 175–177° C.; MS m/e 514 (M+);

Analysis for: $C_{19}H_{13}Br_2ClO_5$ Calc'd: C, 44.18; H, 2.54. Found: C, 44.16; H, 2.46

EXAMPLE 21

[4-(2-benzyl-benzo[b]thiophen-3-carbonyl)-2,6-dibromo-phenoxymethyl]-phosphonic acid Sodium hydride (0.09 g, 80% in mineral oil) was added into a cold (0° C.) mixture of (2-benzyl-benzo[b]thiophen-3-yl)-(3,5-dibromo4-hydroxy-phenyl)-methanone (0.96 g, 1.91 mmol), and tetrahydrofuran (20 mL). The mixture was stirred for 1 hour and then diethyl trifluoromethanesulfonoxymethylphosphonate (0.63 g) was added dropwise. The new mixture was allowed to come to room temperature, stirred for 4 hours, and then warmed to 50° C. and stirred for 2 additional hours. The mixture poured into water and extracted with ethyl acetate. The organic extracts were dried over MgSO$_4$. Purification be flash chromatography (dichloromethane/acetonitrile 95:5) gave a brown oil (0.79 g, 63% yield). The product was taken in dichloromethane (18 mL) and treated at 0° C. with iodotrimethylsilane (0.45 mL) for 6 hours. The mixture was poured into water and extracted with ethyl acetate. The organic extracts were dried over MgSO$_4$. Evaporation and purification by flash chromatography (dichloromethane/acetonitrile 85:15) gave a yellow solid (1.1 g, 77% yield): mp 210–212° C.; MS m/e 595 (M+H)+;

EXAMPLE 22

(R)-2-[2,6-dibromo-4-(2-butyl-benzofuran-3-carbonyl)-phenoxy]-3-phenyl-propionic acid Diethylazodicarboxylate (0.13 mL) was added dropwise into a solution of (2-butyl-benzofuran-3-yl)-(3,5-dibromo-4-dihydroxy-phenyl)-methanone (0.24 g, 0.54 mmol), triphenylphosphine (0.21 g), (S)-(–)-3-phenyllactic acid methyl ester (0.14 g), and benzene (2.4 mL). The mixture was stirred at 80° C. for 3 hours and at room temperature overnight. The volatiles were removed in vacuo and the residue was purified by flash chromatography to give a oil (0.13 g). The product was dissolved in tetrahydrofuran (1.7 mL) and methyl alcohol (1.7 mL) and treated with potassium hydroxide (1.0 N, 0.5 mL). After stirring for 4 hours the mixture was poured into water, acidified aith HCl (1 N) and extracted with ethyl ether. The organic extracts were dried over MgSO$_4$. Evaporation gave a light yellow solid (0.23 g, 84% yield): mp 56–58° C.; MS m/e 597 (M–H)+;

Analysis for: $C_{28}H_{24}Br_2O_5 \times 0.8 H_2O$ Calc'd: C, 54.69; H, 4.20. Found: C, 54.65; H, 3.88

EXAMPLE 23

(R)-2-[2,6-dibromo-4-(2-butyl-benzofuran-3-ylmethyl)-phenoxy]-3-phenyl-propionic acid This compound was prepared from 2,6-dibromo-4-(2-ethyl-benzofuran-3-yl-methyl)-phenol and (S)-(–)-3-phenyllactic acid methyl ester in substantially the same manner, as described in Example 21, and was obtained as an oil (0.11 g 91% yield). The product was treated with 1N sodium hydroxide (0.19 mL) in methyl alcohol for 30 minutes. Evaporation gave a white solid (0.1 g, 84% yield): mp 225–226° C.; MS m/e 583 (M–H)+;

Analysis for: $C_{28}H_{25}Br_2O_4Na \times 0.3 H_2O$ Calc'd: C, 54.78; H, 4.20. Found: C, 54.60; H, 3.79

What is claimed is:

1. A compound of formula I having the structure

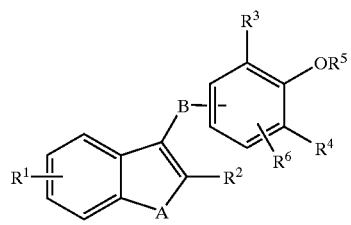

I wherein

A is O, or S;

B is —(CH$_2$)$_m$—, —CH(OH)—, or carbonyl;

R$^1$ is hydrogen, nitro, halogen, alkyl of 1–6 carbon atoms, alkoxy of 1–6 carbon atoms, or trifluoromethyl;

R$^2$ is Het-alkyl wherein the alkyl moiety is 1–6 carbon atoms;

Het is

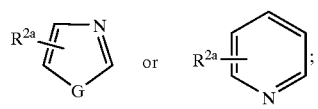

R$^{2a}$ is alkylene of 1–3 carbon atoms;

G is oxygen, sulfur, or nitrogen;

R$^3$, R$^4$ are each, independently, hydrogen, halogen, alkyl of 1–3 carbon atoms, aryl of 6–10 carbon atoms or a heterocyclic ring of 5 to 7 ring atom containing 1 to 3 heteroatoms selected from oxygen, nitrogen, sulfur;

R$^5$ is hydrogen, alkyl of 1–6 carbon atoms, —CH(R$^7$)R$^8$, —C(CH$_2$)$_n$CO$_2$R$^9$, —C(CH$_3$)$_2$CO$_2$R$^9$, —CH(R$^7$)(CH$_2$)$_n$CO$_2$R$^9$, or CH(R$^7$)C$_6$H$_4$CO$_2$R$^8$;

$R^6$ is hydrogen, halogen, alkyl of 1–6 carbon atoms, or —$OR^5$;

m=1–6;

n=1–6;

$R^7$ is hydrogen, alkyl of 1–6 carbon atoms, aryl of 6–10 carbon atoms, or arylalkyl of 7–15 carbon atoms;

$R^8$ is —$CO_2R^{10}$, —$CONHR^{10}$, tetrazole, or —$PO_3$;

$R^9$ and $R^{10}$ are each, independently, hydrogen, alkyl of 1–6 carbon atoms, aryl of 6–10 carbon atoms, or arylalkyl of 7–15 carbon atoms;

or a pharmaceutically acceptable salt thereof.

2. A pharmaceutical composition, which comprises a compound of formula I having the structure

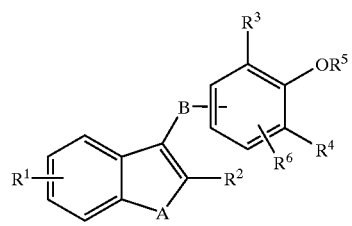

I wherein:

A is O, or S;

B is —$(CH_2)_m$—, —CH(OH)—, or carbonyl;

$R^1$ is hydrogen, nitro, halogen, alkyl of 1–6 carbon atoms, alkoxy of 1–6 carbon atoms, or trifluoromethyl;

$R^2$ is Het-alkyl wherein the alkyl moiety is 1–6 carbon atoms;

Het is

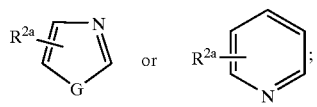

$R^{2a}$ is alkylene of 1–3 carbon atoms;

G is oxygen, sulfur, or nitrogen;

$R^3$, $R^4$ are each, independently, hydrogen, halogen, alkyl of 1–3 carbon atoms, aryl of 6–10 carbon atoms or a heterocyclic ring of 5 to 7 ring atom containing 1 to 3 heteroatoms selected from oxygen, nitrogen, sulfur;

$R^5$ is hydrogen, alkyl of 1–6 carbon atoms, —$CH(R^7)R^8$, —$C(CH_2)_nCO_2R^9$, —$C(CH_3)_2CO_2R^9$, —$CH(R^7)(CH_2)_nCO_2R^9$, or $CH(R^7)C_6H_4CO_2R^9$;

$R^6$ is hydrogen, halogen, alkyl of 1–6 carbon atoms, or —$OR^5$;

m=1–6;

n=1–6;

$R^7$ is hydrogen, alkyl of 1–6 carbon atoms, aryl of 6–10 carbon atoms, or arylalkyl of 7–15 carbon atoms;

$R^8$ is —$CO_2R^{10}$, —$CONHR^{10}$, tetrazole, or —$PO_3$;

$R^9$ and $R^{10}$ are each, independently, hydrogen, alkyl of 1–6 carbon atoms, aryl of 6–10 carbon atoms, or arylalkyl of 7–15 carbon atoms;

or a pharmaceutically acceptable salt thereof, and a pharmaceutical carrier.

* * * * *